United States Patent [19]

Durkan

[11] Patent Number: 5,301,683
[45] Date of Patent: Apr. 12, 1994

[54] DIAGNOSING CARPAL TUNNEL SYNDROME

[76] Inventor: John A. Durkan, 902 12th St., Hood River, Oreg. 97031

[21] Appl. No.: 813,210

[22] Filed: Dec. 23, 1991

[51] Int. Cl.$^5$ ............................................. A61B 5/103
[52] U.S. Cl. .................................... 128/744; 128/774; 606/201
[58] Field of Search ............... 128/774, 782, 898, 630, 128/645, 652, 676, 677, 686, 744, 748; 606/201, 202, 203

[56] References Cited

U.S. PATENT DOCUMENTS

| | | | |
|---|---|---|---|
| 3,680,386 | 8/1972 | Cannon | 73/379 |
| 4,774,966 | 10/1988 | Lemmen | 128/774 |
| 4,883,073 | 11/1989 | Aziz | 128/878 |
| 4,899,763 | 2/1990 | Sebastian et al. | 128/878 |
| 4,941,460 | 7/1990 | Working | 128/77 |
| 4,966,137 | 10/1990 | Davini | 128/87 R |
| 5,012,817 | 5/1991 | Zeilinski et al. | 128/744 |
| 5,048,536 | 9/1991 | McEwen | 128/748 |
| 5,107,853 | 4/1992 | Plyter | 128/774 |
| 5,131,408 | 7/1992 | Smith | 128/774 |
| 5,133,734 | 7/1992 | Lee | 606/201 |

FOREIGN PATENT DOCUMENTS 3803552  6/1989  Fed. Rep. of Germany ...... 128/774

OTHER PUBLICATIONS

Callister, Jr. "Mechanical Properties of Metals: Hardness" from *Materials Science and Engineering* John Wiley & Sons, Inc. New York 1985, pp. 98–103.

"Testing for Carpal Tunnel Syndrome" *The Lancet*, vol. 338, pp. 479–480, Aug. 24, 1991.

"Verification of the Pressure Provocative Test in Carpal Tunnel Syndrome" by Tara M. Williams, M. D. et al. pp. 8–11, 1992.

Letter from Dr. med. Otto Jungo to Dr. John Durkan, 1 page, Feb. 17, 1992 enclosing "Eine einfache Prufung zum Nachweis des Karpaltunnelsyndroms" *Manuelle Medizin*, 2 pages, Mar. 1969.

"Median Nerve Compression Test in Carpal Tunnel Syndrome Diagnosis Reproduces Signs and Symptoms in Affected Wrist" *Orthopaedic Review*, by D. Paley, M. D. et al. vol. XIV, No. 7, pp. 41–45, Jul. 1985.

"Provocative Sensory Testing in Carpal Tunnel Syndrome" by C. B. Novak et al. *Journal of Hand Surgery*, pp. 204–204, British Vo. 1992.

Durkan, "A New Diagnostic Test for Carpal Tunnel Syndrome," *The Journal of Bone and Joint Surgery* 73:535–538 (Apr. 1991).

Gelberman et al., "The Carpal Tunnel Syndrome," *The Journal of Bone and Joint Surgery* 63-A:380–383 (1981).

Gelberman et al., "Sensibility Testing in Peripheral–Nerve Compression Syndromes," *The Journal of Bone and Joint Surgery* 65-a:632–638 (1983).

Lundborg et al., "Median nerve compression in the (List continued on next page.)

Primary Examiner—Stephen C. Pellegrino
Assistant Examiner—Guy V. Tucker
Attorney, Agent, or Firm—Klarquist, Sparkman, Campbell, Leigh & Whinston

[57] ABSTRACT

An improved method and device are disclosed for diagnosing carpal tunnel syndrome. Direct pressure is applied to the median nerve as it passes through the carpal tunnel at the base of the wrist. Application of 100–200 mm mercury pressure to the nerve for thirty seconds produces numbness and paresthesias in the distribution of the median nerve distal to the carpal tunnel in patients having anatomic evidence of carpal tunnel syndrome. The disclosed device is a clamp having an opposing wrist support member and pressure application member. The distance between the support and pressure application members can be varied to alter the amount of pressure applied to the median nerve in the carpal tunnel. Use of the disclosed method and device provides a much more sensitive and specific clinical test for carpal tunnel syndrome than could previously be obtained with Phalen's test or Tinel's sign. Clinical use of this test can, in some cases, eliminate the need for electromyographic studies.

10 Claims, 3 Drawing Sheets

OTHER PUBLICATIONS carpal tunnel-Functional response to experimentally induced controlled pressure," *The Journal of Hand Surgery* 7:252–259.

Gellman et al., "Carpal Tunnel Syndrome," *The Journal of Bone and Joint Surgery* 68-A:735–737 (1986).

Retractors catalogue, pp. E42, E41, E31, E28, C64, A146, Author unknown. Date unknown.

Ametak catalogue "Force Measurement Products-A Complete Line of Force Gauges, Test Stands & Accessories." Date unknown.

Mechanical Force Gauges (catalogue). Date unknown, author unknown.

Universal Testing Machines (catalogue) Date unknown. Author unknown.

Accessories and Adapters (catalogue) Date unknown. Author unknown.

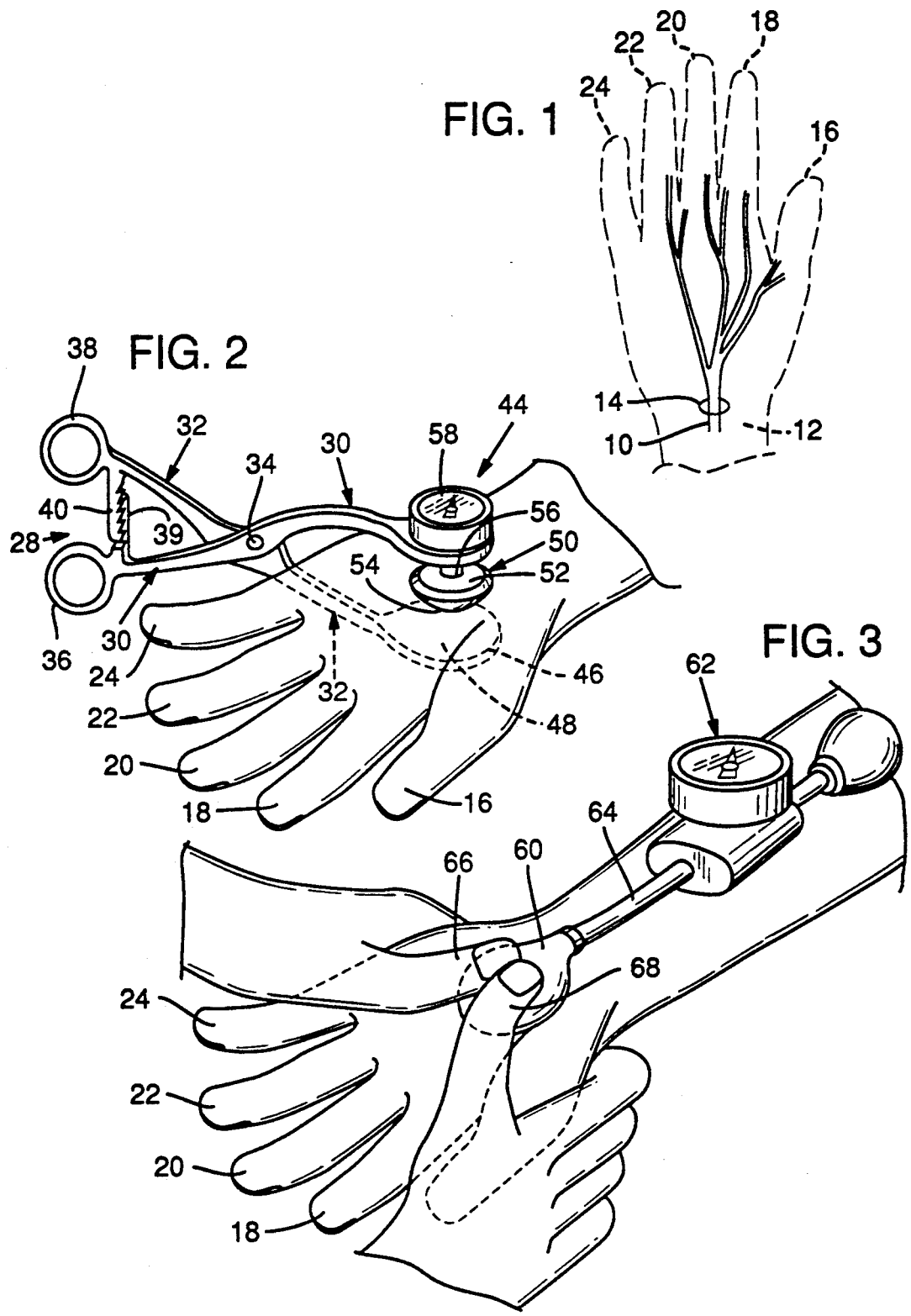

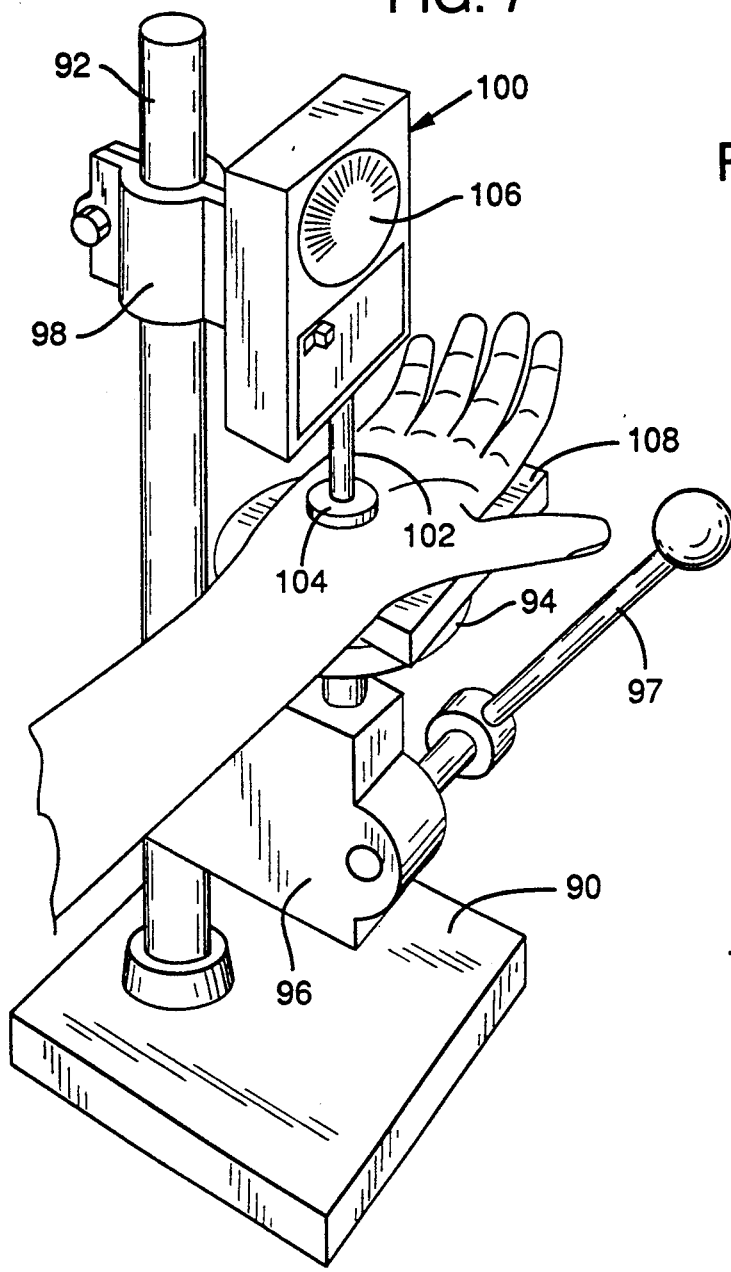
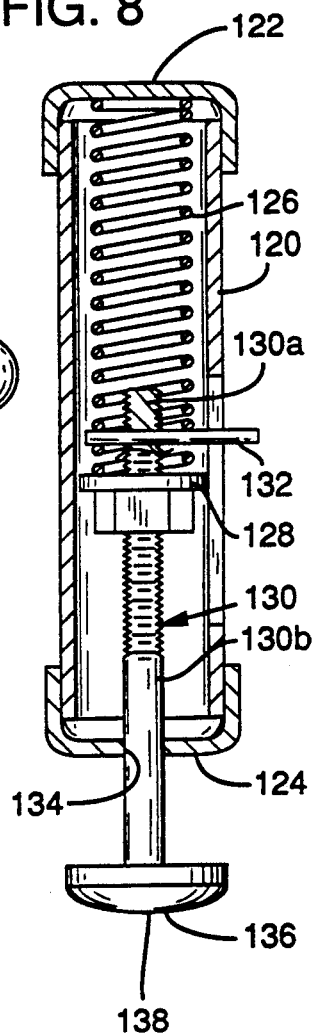

DIAGNOSING CARPAL TUNNEL SYNDROME

1. FIELD OF THE INVENTION

This invention concerns a method and device for diagnosing carpal tunnel syndrome.

2. GENERAL DISCUSSION OF THE BACKGROUND

Carpal tunnel syndrome is a common problem that continues to increase in incidence. Symptoms of the syndrome include motor weakness and sensory loss in areas of the hand innervated by the median nerve. Such symptoms include paresthesias, burning or tingling in the radial-palmar aspect of the hand (the thumb and adjacent fingers), and pain in the wrist, palm or even the forearm. Sensory deficits such as numbness may occur in the palmar aspect of the first three digits and motor symptoms such as weakness or inability to oppose the thumb and fingers may follow. The syndrome may occur in one or both hands, and occurs more frequently in women than in men. The syndrome often occurs in people who use their hands for repetitive motions, such as typing, computer data entry, housepainting, carpentry, and associated occupations.

Carpal tunnel syndrome is believed to be caused by compression of the median nerve that supplies sensation to the thumb, index finger, middle finger and radial half of the ring finger. The nerve passes through the wrist beneath the flexor retinaculum or transverse carpal ligament that overlies and protects the wrist just below the palm. The transverse carpal ligament and tendons of the flexor muscles define a tunnel through which the median nerve passes. If the nerve becomes swollen as it passes through the carpal tunnel, or if the carpal ligament becomes abnormally thickened, the nerve may be compressed and function abnormally.

Previous studies have been performed to assess the effects of elevated pressure on the median nerve in the carpal tunnel. Gelberman et al. used the wick-catheter technique to measure changes in pressure with the wrist in various positions. Patients who had carpal tunnel syndrome had mean pressures of ninety-nine millimeters of mercury (13.2 kilopascals) with the wrist flexed and 110 millimeters of mercury (14.7 kilopascals) with the wrist extended. For control subjects, the measurements were thirty-one millimeters of mercury (4.1 kilopascals) with the wrist flexed and thirty millimeters of mercury (4 kilopascals) with the wrist extended.

Lundborg et al., *J. Hand Surg.* 7:252-259 (1982) studied the effects of prolonged compression of the median nerve in sixteen volunteers who had no history of carpal tunnel syndrome. Compression with pressure of thirty to ninety millimeters of mercury (4 to 12 kilopascals) for thirty to ninety minutes produced abnormal delays in nerve conduction and abnormal two-point discrimination. These investigators and others have theorized that compression produces ischemia of the median nerve, resulting in paresthesias and reversible failure of nerve conduction. The earlier indicator of impaired function of a nerve due to compression was a delay in sensory conduction.

Gellman et al., *J. Bone and Joint Surg.* 68A:735-737 (1986) performed sensibility testing with the Semmes-Weinstein monofilament test in patients who had carpal tunnel syndrome. They found the sensitivity of the test to be 91%, but they also found a 21% rate of false-positive results in a normal control population.

An accurate diagnosis of carpal tunnel syndrome must be made if appropriate treatment is to be obtained. It is critical, for example, to distinguish carpal tunnel syndrome from a C6 root compression due to cervical osteoarthropathy. Symptoms resembling carpal tunnel syndrome can also accompany neuromuscular disease, cerebral damage, peripheral neuropathy, or may be psychogenic in origin. Up to the present time, diagnosis of the syndrome has been made using Phelan's Test, Tinel's Sign, and electromyographic nerve conduction studies.

Phelan's Test requires that the patient's wrist be held in acute flexion for sixty seconds, or that the patient presses the back of both hands together to form right angles. If numbness and tingling develop over the distribution of the median nerve, the sign is positive and carpal tunnel syndrome is suspected. To elicit Tinel's Sign, an examiner lightly percusses the course of the median nerve in the carpal tunnel for several seconds without exerting sustained pressure. A tingling or electric sensation in the distribution of the median nerve is a positive test that additionally suggests carpal tunnel syndrome.

Phelan's maneuver and Tinel's Sign, however, are of limited diagnostic value. Although they suggest the presence of the syndrome, the diagnosis must be confirmed by expensive electromyographic (EMG) nerve conduction studies that measure the velocity of nerve conduction through the carpal tunnel. Reduced sensory and motor conduction velocity is associated with carpal tunnel syndrome. An EMG diagnosis is sensitive enough to detect the syndrome in 85% of patients, but a normal EMG study can still occur in patients who have anatomic evidence of a median nerve compression.

The value of a screening test is judged by its sensitivity and specificity. The sensitivity of a test measures the likelihood of a positive result in patients known to have the disease. Conversely, specificity is the likelihood of a negative result in patients known to be free of the disease. Previous studies have shown that the sensitivity and specificity of the Phelan's and Tinel's tests are relatively low, such that expensive EMG studies are required to make an accurate diagnosis. Even the more sophisticated EMG studies, however, have a sensitivity of only about 85%. Hence, there is a need in clinical medicine for a quick screening test that will accurately diagnose carpal tunnel syndrome.

It is accordingly an object of this invention to provide an improved, inexpensive, sensitive test for screening patients who are complaining of the symptoms of carpal tunnel syndrome.

It is another object of the invention to provide such an improved test that will be more specific for diagnosing carpal tunnel syndrome in those patients who have anatomic nerve compressions, without also being positive for a large number of patients who do not have anatomic evidence of the syndrome.

Yet another object of the invention is to help reduce medical costs by providing an improved clinical screening test that can quickly be performed in an office setting without resort to expensive electromyographic studies.

It is also an object of the invention to provide a device that is suitable for performing the improved test.

These and other objects of the invention will be better understood by reference to the following drawings and detailed description.

SUMMARY OF THE INVENTION

The foregoing objects are achieved by providing a provocative test for diagnosing carpal tunnel syndrome. In this test, an examiner applies direct sustained pressure externally to the wrist of a patient who is complaining of symptoms of the syndrome. Pressure is exerted over the expected anatomic pathway of the median nerve through the carpal tunnel, and the patient is asked to report the onset of any numbness, pain or paresthesias or weakness in the distribution of the median nerve distal to the level of the carpal tunnel.

Direct compression of the nerve need only occur for less than a minute, preferably for at least about 30 seconds. In some preferred embodiments, about 100-200 mm Hg pressure is applied using a bulb nanometer device applied externally to the wrist to evoke the symptoms. This would be equivalent to a compression pressure ranging from 2-10 psi. In more preferred embodiments, a bulb pressure of 150 mm Hg would be used, or 4-8 psi. In more preferred embodiments, a pressure of 6-8 psi is applied externally to the wrist to evoke the symptoms. This pressure can be applied either with an examiner's thumbs, with a bulb that measures pressure exerted through the bulb on the wrist, or with a clamp having a gauge for measuring the amount of pressure exerted on the wrist.

A preferred embodiment of such a diagnostic device includes a pressure member for compressing the median nerve and an opposing pressure member for stabilizing the clamp on the wrist. A gauge connected to the pressure member measures the pressure applied to the wrist to help provide repeatability of results in screening for carpal tunnel syndrome.

In especially preferred embodiments, the distance between the pressure and support members can be selectively varied for calibrating the amount of pressure applied by the clamp. In one preferred embodiment, the clamp resembles a forceps having pivotally connected legs, each of which carries a ratchet bar that selectively inter-engages the opposing ratchet to hold the pressure and support members at a selected distance from one another. A C-clamp embodiment is also disclosed. In yet another embodiment, the hand is placed on a platform that can be raised or lowered to move the palm toward or away from a pressure applicator.

BRIEF DESCRIPTION OF THE DRAWINGS

FIG. 1 is a schematic view showing the pathway of the median nerve through the carpal tunnel, and the distribution of that nerve to the palm and fingers of a hand.

FIG. 2 is a perspective view showing a forceps-like embodiment of the clamp of the present invention applying pressure to the median nerve as it passes through the carpal tunnel.

FIG. 3 is an alternative embodiment of the invention showing a pressure bulb attached to a pressure gauge for monitoring the amount of force exerted by an examiner's fingers on a patient's wrist.

FIG. 7 is a perspective view of another embodiment of the invention in which the hand is placed on a movable platform.

FIG. 8 is a cross-sectional view of yet another embodiment of the tester.

DETAILED DESCRIPTION OF PREFERRED EMBODIMENT

Figure 6:
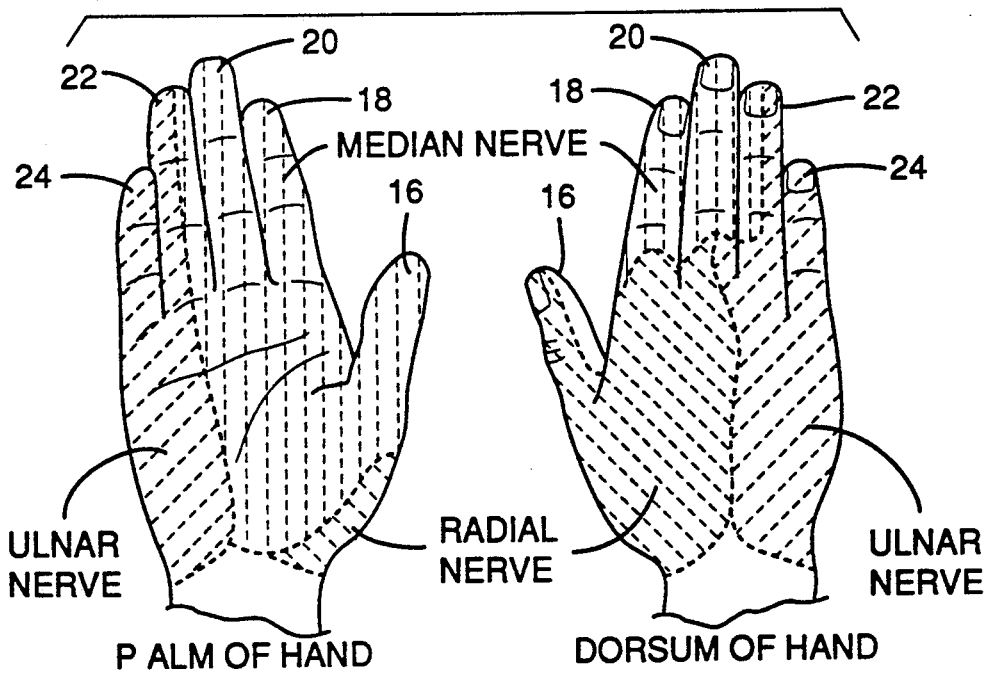
FIG. 6 is a schematic view of the sensory cutaneous innervation of the hand.

The expected pathway and distribution of the median nerve 10 through the wrist 12 is shown schematically in FIG. 1. The nerve 10 passes through the flexor retinaculum at circled portion 14 and divides into branches to the palmar aspect of the thumb 16, as well as the anterior and dorsal aspects of the index finger 18, middle finger 20 and one half of ring finger 22. It provides no sensory innervation to little finger 24. The sensory cutaneous distribution of the median nerve is shown schematically in FIG. 6.

In accordance with the method of the present invention, direct external pressure is applied over the median nerve in the region 14 of wrist 12 as the nerve passes through the flexor retinaculum. Preferably 100-200 mm Hg of pressure, most preferably 150 mm Hg is applied to the wrist for thirty seconds at region 14 through a sphygmomanometer bulb, as shown in FIG. 3. Alternatively, mechanical applicators apply 1-8 psi pressure to the same area. Development of sensory defects in the distribution of the median nerve (FIG. 6) after thirty seconds of compression is a sensitive and specific sign of carpal tunnel syndrome. Motor weakness in the thenar muscles or lumbricals of the second and third digits is also a positive sign that suggests the syndrome is present.

One embodiment of an instrument 28 that is suitable for performing the diagnostic test of the present invention is shown in FIG. 2. The instrument 28 resembles a surgical clamp that includes two pivotally connected legs 30, 32. Each of legs 30, 32 is slightly S-shaped, with enlarged central portions that reciprocally slide against one another and are pivotally fixed together by a pivot 34. A handle end of each leg 30, 32 terminates in a finger loop 36, 38 through which an operator's finger and thumb can respectively be placed. Inter-engaging ratchet members 39, 40 project respectively from legs 30, 32 adjacent loops 36, 38 and extend toward one another. Serrated ratchets project from adjoining faces of members 39, 40 such that the inter-engaging ratchets can lock legs 30, 32 into selected position relative to one another.

When ratchet members 39, 40 are not engaged, legs 30, 32 are substantially co-planar. As leg 32 pivots toward leg 30, however, the serrated ratchets bias the handle end of leg 32 toward leg 30 and out of the common plane such that leg 32 is disposed at a small angle to leg 30. This angle between the legs locks the ratchets into engagement with one another, and fixes the legs a set or preselected distance from one another. The distance between the legs can be selectively reduced by forcing loops 36, 38 toward each other to advance progressively the ratchets on member 40 over the ratchets on member 38. The legs will lock at incremental positions corresponding to alignment of overlapping interlocking serrations. The ratchets can be selectively disengaged, however, by pushing on the handle end of the legs to force the ratchets away from each other and once again allow free pivotal movement of the legs relative to each other.

Opposite the handle end of each leg 30, 32 is a pressure application end. The pressure application end of leg 30 carries a pressure member 44 that applies pressure along an arc defined by the pressure end of leg 30 as leg 30 pivots around pivot 34. Member 44 is designed to apply pressure to the median nerve as it passes through the carpal tunnel. The pressure application end of leg 32, in contrast, is a wrist support stabilizer 46. The stabilizer 46 is an enlarged paddle having a broad, flattened surface 48 that is substantially co-planar with the long axis of leg 32 and perpendicular to the arc along which member 44 applies pressure. The shape of paddle 46 is shaped to rest against the dorsal aspect of a wrist, as shown in FIG. 2. In preferred embodiments, surface 48 of the paddle is padded to provide comfort to the patient during the diagnostic procedure.

The pressure member 44 carried by leg 30 includes a foot pad 50 having any shape suitable for applying pressure against the median nerve as it passes through the carpal tunnel. In the embodiment shown in FIG. 2, the foot pad is a conical member having an enlarged flat base 52 that tapers to a rounded point 54 for applying pressure against the nerve. Foot pad 50 is free to reciprocate along an axis through a connector rod 56, which communicates with a fixed conventional pressure gauge 58. Gauge 58 is calibrated such that the pressure applied against the median nerve by foot pad 50 is translated into a pressure reading, such as pounds per square inch (psi). The gauge allows reproducible amounts of pressure to be applied to the median nerve in sequential patients, such that reproducibility of clinical results is achieved.

In operation, ratchet members 38, 40 are disengaged such that legs 30, 32 are free to pivot relative to one another about pivot 34. The jaw of the pressure application end of instrument 28 is enlarged by moving handle loops 36, 38 through an arc away from one another. Paddle 46 and pressure member 44 correspondingly move apart through an arc until the distance between them is great enough to allow the wrist of a patient to fit between the paddle and pressure member. The instrument is positioned with paddle 48 flat against the dorsal aspect of the patient's wrist, and with the tip of foot pad 50 positioned over region 14 (FIGS. 1 and 2) which marks one location of the expected anatomic path of the median nerve through the carpal tunnel. Region 14 is approximately at the median aspect of the base of the palm. Handle loops 36, 38 are then moved toward one another such that the ratchet or members 38, 40 incrementally engage to selectively fix paddle 46 and foot pad 54 at incrementally closer distances to each other. The jaw of the instrument continues to close until the pressure reading on gauge 58 reaches a desired level, for example 3 psi.

When approximately the desired amount of pressure registers on the gauge, ratchets 38, 40 are inter-engaged to lock the instrument in position with the desired amount of external pressure applied to the median nerve. Thirty seconds after the desired pressure is applied, the patient is asked to describe any changes in sensation or motor function of the hand to which the clamp has been applied. Specific inquiry is made, for example, as to the presence of any numbness or paresthesias in the distribution of the median nerve shown in FIG. 6, and specifically whether any such sensations are felt in thumb 16, fingers 18, 20 or the half of finger 22 adjacent finger 20. A report of any of these symptoms constitutes a positive test that strongly indicates the presence of an anatomic nerve compression of the type found in carpal tunnel syndrome.

An alternative embodiment of the device is shown in FIG. 3 where direct compression of the median nerve 10 running deep to the flexor retinaculum is accomplished with a rubber atomizer bulb 60 connected to a pressure manometer of the type conventionally found in sphygmomanometers. A suitable bulb would be a Tycos ® sphygmomanometer bulb. The pressure in bulb 60 is communicated to manometer 62 by conventional pressure tubing 64. Using this device, an examiner's thumbs 66, 68 can both be placed on bulb 60 and the amount of manual pressure calibrated to a desired level by watching gauge 62. In the disclosed embodiment, a pressure of 150 mm of mercury (20 kilopascals, or about 2.9 psi) is applied to the carpal tunnel for less than a minute, preferably as long as thirty seconds.

Figure 4:
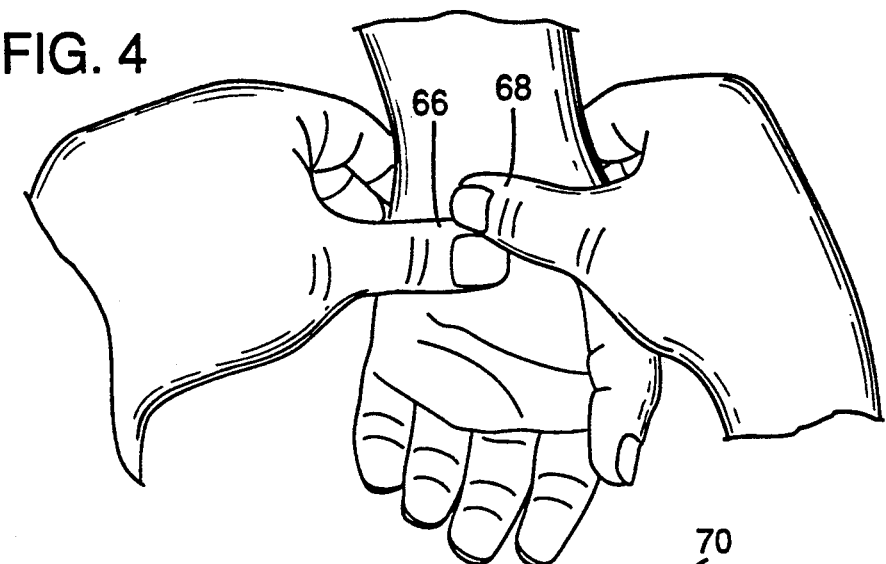
FIG. 4 is a view of another embodiment of the invention in which direct digital pressure is applied to the wrist by an examiner.

Another alternate method of performing the test is shown in FIG. 4, in which the examiner's thumbs 66, 68 exert even pressure longitudinally along the expected anatomic pathway of the median nerve 10 as the nerve passes through the carpal tunnel. The device shown in FIG. 3 can serve as a training tool that helps the examiner develop sufficient kinesthetic sense to accurately estimate the level of pressure thumbs 66, 68 are applying to the patient's wrist. Once this kinesthetic sense has been refined, direct digital application of pressure can be performed as in FIG. 4.

Figure 5:
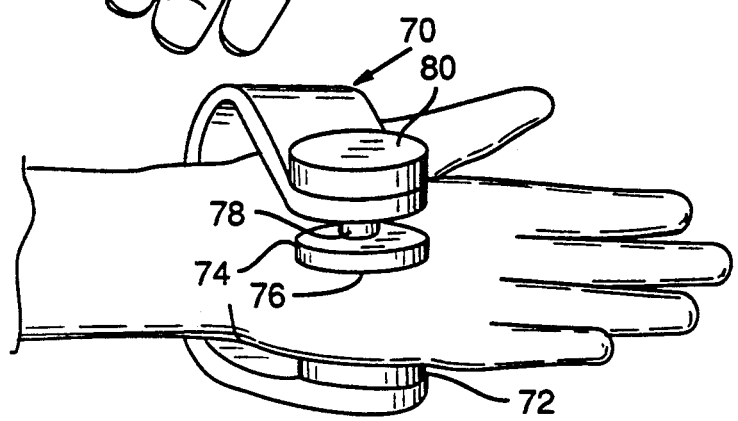
FIG. 5 is a perspective view of yet another embodiment of the clamp of the present invention.

Yet another embodiment of the device for performing this diagnostic test is shown in FIG. 5. In this embodiment, the device is a C-clamp 70 that terminates in opposing top and bottom jaws. A padded wrist support 72 is carried by the bottom jaw and foot pad 74 is carried by the top jaw. The foot pad 74 has an enlarged, circular one square inch area face 76 that fits against the base of the palm. Foot pad 74 tapers in a direction away from the wrist toward the upper jaw until it forms a reciprocal rod 78. Rod 78 communicates with a pressure transducer or gauge 80 that translates the pressure exerted against median nerve 14 into a calibrated reading. The pressure exerted by foot pad 74 against the wrist is varied by altering the distance between the top and bottom jaws using an operating screw (not shown).

Another embodiment of a pressure application device is shown in FIG. 7, wherein a patient's hand is placed on a movable platform to move it toward and away from a pressure transducer. The device includes a heavy base 90 which rests upon a solid surface and provides a support for an upright post 92. A movable platform 94 is reciprocally mounted on a platform support 96 that is clamped to post 92. Platform 94 is raised and lowered by lever 97, as in a conventional drill press. A transducer support clamp 98 is secured to post 92 above support 96, and holds a pressure transducer 100 above platform 94. The transducer 100 can be any of a variety of devices, for example an electronic force gauge such as the Accuforce Electrim ™ Gauge from Ametek, a division of Mansfield & Green. The gauge has a downwardly projecting loading arm 102 that terminates in pressure application button 104 having a lower face with a surface area of 0.7 square inch that abuts the patient's lower palm area. A digital dial 106 displays the amount of pressure exerted against button 104.

In operation, a comfortable hand support 108 is placed on platform 94 and the patient's hand placed palm up on the support with button 104 positioned over the pathway of the median nerve through the carpal tunnel. Lever 97 is then pulled down to raise platform 94 and progressively force the patient's palm against button 104 until a desired force is displayed on digital display 106. The force is then maintained for a desired period of time, then discontinued by raising lever 97 to lower platform 94.

Yet another embodiment of a tester is shown in FIG. 8, and includes a tubular housing 120 with top and bottom caps 122, 124. A longitudinal slot is provided in the wall of housing 120, beside which appear spaced calibrated indicia (for example from 2 to 10 psi, 103 to 517 mm Hg). A spring 126 fits within housing 120, and extends between cap 128 and a movable pressure plate 128. A rod 130 extends through plate 128, such that the rod comprises a top portion 130a and a bottom portion 130b. Top portion 130a carries a perpendicular pin 132 to gauge the degree of compression of spring 126. Bottom portion 130b extends through a circular opening 134 in cap 124 and protrudes beyond cap 124 before terminating in a pressure application button 136. The arcuate surface 138 of button 136 has a surface area of about 0.8 in$^2$.

In operation, surface 138 of button 136 is placed over the expected anatomic pathway of the median nerve through the carpal tunnel. A sufficient amount of pressure is applied to compress spring 126 until pin 136 moves to a calibrated position that indicates a desired pressure is being applied to the wrist for a sufficient period of time.

Diagnostic Method and Case Histories

Thirty-one subjects with idiopathic carpal tunnel syndrome were studied. The condition involved both hands in fifteen of them. The study population consisted of eight men and twenty-three women, who ranged in age from twenty-two to seventy-nine years (average age, forty-five years). Carpal tunnel syndrome was suspected in these subjects because they complained of pain, numbness, and paresthesias in the distribution of the median nerve. The Phalen test, the Tinel test, and the direct compression test of the present invention were performed on all of these subjects.

The direct external compression test consists of direct compression of the median nerve running deep to the flexor retinaculum. Pressure was applied to the area of the carpal tunnel for as long as thirty seconds with a device that was constructed by connection of a rubber atomizer-bulb to a pressure manometer from a sphygmomanometer (FIG. 3). Pressure within the bulb that was measured by the manometer was a pressure of 150 millimeters of mercury (twenty kilopascals, or 2.9 psi). Alternatively, the examiner exerted even pressure to the median nerve in the carpal tunnel with both thumbs (FIG. 4). The interval from the application of compression to the onset of numbness, pain, or paresthesias in the distribution of the median nerve distal to the level of the carpal tunnel was recorded.

All thirty-one patients selected for this study had characteristic symptoms of carpal tunnel syndrome and definite abnormalities of nerve conduction velocity in one or both hands. Thus, the study group consisted of forty-six symptomatic hands for which electrodiagnostic findings had been positive. Positive electrodiagnostic findings are often considered diagnostic of carpal tunnel syndrome. One hand of each of fifty asymptomatic control subjects was also evaluated with the Phalen test, the Tinel test, and the carpal compression test of the present invention. In forty-four (96%) of the forty-six symptomatic hands, the motor conduction latency of the median nerve was abnormal, and in forty-two (91%) the sensory latency of the median nerve was abnormal. In forty (87%) of the symptomatic hands, both motor and sensory conduction were abnormal.

For forty (87%) of the forty-six symptomatic hands, the result of the new test was positive (Table I), with the average time to the onset of symptoms being sixteen seconds (range, five to twenty-nine seconds). The results (the number of positive responses and the time-interval to the onset of symptoms) were identical for the subjects who were tested with application of 150 millimeters of mercury (twenty kilopascals) of pressure with the bulb manometer and for those who were tested with application of direct pressure to the area of the carpal tunnel by the thumbs of the examiner.

TABLE I

| | Results | | | | | | | |
|---|---|---|---|---|---|---|---|---|
| | Group That Had Carpal Tunnel Syndrome | | | Control Group | | | | |
| Test | Pos./Neg. (No.) | Interval* (secs.) Avg. | Range | Pos./Neg. (No.) | Interval* (secs.) Avg. | Range | Sensitivity (Per cent) | Specificity (Per cent) |
| Carpal compression | 40/6 | 16 | 5-29 | 5/45 | 24 | 16/28 | 87 | 90 |
| Phalen | 32/14 | 25 | 5-45 | 8/42 | 44 | 26-55 | 70 | 84 |
| Tinel | 26/20 | — | — | 10/40 | — | — | 56 | 80 |

*The intervals were recorded for abnormal (positive) determinations.

The Phalen wrist flexion test was positive for thirty-two (70%) of the forty-six symptomatic hands, and the average interval to the onset of symptoms was twenty-five seconds (range, five to forty-five seconds). The Tinel percussion test was positive for twenty-six (56%) of the forty-six symptomatic hands.

Of the forty hands for which the carpal compression test was positive, thirty-one had a positive Phalen test and twenty-five, a positive Tinel test.

The result of the carpal compression test was negative for six hands, despite the electrodiagnostic findings having been abnormal. In four of these hands, sensory conduction of the median nerve was absent and sensation to pinprick and two-point discrimination were diminished in the distribution of the median nerve. In these four hands, the motor conduction latencies ranged from 4.7 to 10.8 milliseconds.

In the control group of fifty hands, the new test revealed paresthesias of the median nerve in five hands (10%), the Phalen test was positive in eight (16%), and the Tinel percussion test was positive in ten (20%). Of the five subjects for whom the carpal compression test was positive, four had a positive Phalen test, two had a positive Tinel test.

All five subjects with a positive carpal compression test had normal motor and sensory findings on electrodiagnostic studies.

A surgical release of the carpal tunnel was performed in thirty-eight of the forty-six hands in the study group. The surgical release was a procedure in which the flexor retinaculum was divided to diminish pressure in the carpal tunnel. No complications occurred, and the symptoms were completely relieved in all thirty-eight hands. Of the eight remaining hands, two were scheduled for future operative treatment. Surgical release was not performed on the remaining six hands because the patient declined operative treatment or the symptoms responded to conservative measures such as use of a splint at night or occupational modifications. In the operatively treated hands, no abnormal lesions or tumors were found on exploration of the carpal tunnel. All of the surgical patients, however, had a consistent narrowing or an hourglass-type constriction of the median nerve deep to the flexor retinaculum. This anatomic abnormality is characteristic of patients who have carpal tunnel syndrome.

In summary, a combination of tests was used to diagnose carpal tunnel syndrome. For one or both hands of all the patients in the study population, carpal tunnel syndrome was confirmed by a positive result on nerve conduction studies. In these hands, the carpal compression test was 87% sensitive for diagnosing carpal tunnel syndrome. The specificity was 90%, with 10% of the results being false positive.

For six of forty-six hands, the carpal compression test was negative despite the result having been positive on electrodiagnostic testing. For four of the six hands, sensory conduction of the median nerve was absent, and two-point discrimination and sensation to pinprick were diminished in the distribution of the median nerve. A combination of sensory testing and the carpal compression test resulted in 96% sensitivity in patients in whom carpal tunnel syndrome had been proved electrodiagnostically.

The sensitivity of the wrist-flexion (Phalen) test was 70%, the specificity was 84%, and 16% of the results were false positive. The Tinel test was the least sensitive, with a 56% rate of positive findings in patients in whom carpal tunnel syndrome had been confirmed by positive nerve conduction studies. The Tinel percussion test was specific in 80% of the hands, and the rate of false-positive results was 20%.

In this study, five control subjects had a positive result on the new test had normal motor and sensory conduction. Electrodiagnostic studies have been considered the standard for diagnosis of carpal tunnel syndrome. However, false-negative findings on electromyography have been reported for as many as 27% of hands that had a clinical diagnosis of carpal tunnel syndrome. Hence the subjects with a positive direct compression test and negative EMG may have had a false-negative electrical study. The method of the present invention may have, therefore, been able to diagnose subclinical carpal-tunnel syndrome in these five subjects.

In view of the high sensitivity and specificity of the carpal compression test, some patients who have typical signs and symptoms of carpal tunnel syndrome may be identified as candidates for operative treatment and thus avoid the expense and time that electrodiagnostic testing involves. The new test, whether performed with a pressure manometer, clamp, or with direct pressure by the thumbs of the examiner on the flexor retinaculum, is a simple and inexpensive technique for screening for carpal tunnel syndrome.

The specific disclosed embodiment of the test requires direct sustained application of pressure to the median nerve by an instrument or examiner's digit. This contrasts with an indirect increase in pressure on the nerve in Phelan's maneuver, where flexing the wrist physiologically increases carpal pressure. The external pressure is also sustained, unlike the intermittent percussive pressure applied in Tinel's test. Sustained pressure, as used in the following claims, refers to a pressure that is applied constantly without interruption, preferably for a period of at least thirty seconds, most preferably for no longer than thirty or sixty seconds.

In the disclosed embodiment, direct sustained pressure of about 100–200 mm Hg, more preferably 150 mm Hg in the bulb (as measured on the manometer), is applied for thirty seconds. This level of pressure has unexpectedly been found to provide a highly sensitive and specific sign indicating the pressure of anatomic median nerve compression in the carpal tunnel. One would not predict that direct sustained compression of the nerve would provide any greater diagnostic accuracy than the physiological increase in carpal tunnel caused by wrist flexion in Phelan's maneuver. Once the surprising sensitivity and specificity of direct external sustained compression has been appreciated, however, it is within the scope of this invention to screen populations of patients to determine other amounts of external pressure that could be applied. The time period of application could also be varied as the pressure level is varied. It is preferred, however, that the time period not exceed one minute such that the convenience of a quick clinical diagnosis is not diminished.

Pressures measured by the bulb are preferably greater than 100 mm mercury, more preferably 100–200 mm mercury, most preferably about 150 mm mercury. The period of sustained pressure is preferably at least 15 seconds, more preferably 30–60 seconds, most preferably about 30 seconds. The embodiments of FIGS. 2, 5, 7 and 8 preferably measure 2–10 psi applied pressure, more preferably 4–8 psi, and most preferably 6–8 psi.

Having illustrated and described the principles of the invention in several preferred embodiments, it should be apparent to those skilled in the art that the invention can be modified in arrangement and detail without departing from such principles. We claim all modifications coming within the spirit and scope of the following claims.

I claim:

1. A provocative method for diagnosing carpal tunnel syndrome in a patient, comprising the steps of:
   providing a pressure-exerting member connected to a gauge operable to indicate the amount of pressure exerted by such member,
   applying said pressure-exerting member externally to the wrist of the patient over the anatomic pathway of the median nerve through the carpal tunnel of the patient with a clamp that fits around the wrist including a support member that stabilizes the clamp on the wrist and an adjustment member that selectively varies the pressure applied to the wrist to exert a sustained selected pressure thereagainst in excess of 125 mm of mercury for a time less than one minute, and
   determining whether the patient experiences symptoms of carpal tunnel syndrome within said time.

2. The method of claim 1 wherein the step of applying pressure comprises applying pressure with a C-shaped clamp.

3. The method of claim 1 wherein the step of applying pressure comprises providing an adjustable ratchet that selectively sets the distance between the adjustment and support members to calibrate the amount of pressure applied by the clamp.

4. The method of claim 1 wherein the clamp includes a ratchet that selectively fixes the distance between the support and adjustment members, and the applying step comprises fixing the support member a desired distance from the adjustment member with the ratchet to apply selectively a desired amount of pressure on the wrist.

5. The method of claim 1, wherein said selected pressure is in a range of from 125 to 200 mm of mercury.

6. The method of claim 1, wherein said selected pressure is in a range of from 125 to 500 mm of mercury.

7. A provocative method for diagnosing carpal tunnel syndrome in a patient, comprising the steps of:

providing a pressure-exerting member connected to a gauge operable to indicate the amount of pressure exerted by such member, applying said pressure-exerting member externally to the wrist of the patient over the anatomic pathway of the median nerve through the carpal tunnel of the patient to exert a sustained selected pressure thereagainst in excess of 125 mm of mercury for a time less than one minute by providing a platform in opposed relation to said pressure-exerting member, providing a mover for selectively moving the platform and pressure-exerting member toward each other, supporting the side of the patient's wrist opposite said pressure-exerting member on said platform, and moving said platform and pressure-exerting member toward each other to grip the patient's wrist therebetween to establish said selected pressure, and determining whether the patient experiences symptoms of carpal tunnel syndrome within said time.

8. The method of claim 7, wherein the applying step comprises holding said grip on the patient's wrist to maintain said selected pressure for said time.

9. The method of claim 7, wherein said selected pressure is in a range of from 125 to 200 mm of mercury.

10. The method of claim 7, wherein said selected pressure is in a range of from 125 to 500 mm of mercury.

* * * * *

UNITED STATES PATENT AND TRADEMARK OFFICE
CERTIFICATE OF CORRECTION

PATENT NO. : 5,301,683
DATED     : April 12, 1994
INVENTOR(S) : John A. Durkan

It is certified that error appears in the above-identified patent and that said Letters Patent is hereby corrected as shown below:   On the title page: Item [56] Other Publications

```
           line 5, "204" should read --208--
Column 4, line 64, "38"  should read --39--
Column 5, line 35, "38"  should read --39--
Column 5, line 51, "38"  should read --39--
Column 5, line 58, "38"  should read --39--
```

Signed and Sealed this

Eighteenth Day of October, 1994

Attest:

BRUCE LEHMAN

Attesting Officer         Commissioner of Patents and Trademarks